US009775531B2

(12) United States Patent
Brest Van Kempen et al.

(10) Patent No.: US 9,775,531 B2
(45) Date of Patent: Oct. 3, 2017

(54) SENSOR DEVICE, PROCESSING DEVICE, AND MEASUREMENT SYSTEM FOR ACQUIRING A BIOPOTENTIAL

(71) Applicant: Techmedic Development International B.V., Broek op Langedijk (NL)

(72) Inventors: Rutger Alexander Brest Van Kempen, Noord Scharwoude (NL); Alexander Adriaan Huntelerslag, Zuid-Scharwoude (NL)

(73) Assignee: Techmedic Development International B.V., Broek op Langedijk (NL)

( * ) Notice: Subject to any disclaimer, the term of this patent is extended or adjusted under 35 U.S.C. 154(b) by 532 days.

(21) Appl. No.: 13/946,176

(22) Filed: Jul. 19, 2013

(65) Prior Publication Data

US 2013/0303871 A1   Nov. 14, 2013

Related U.S. Application Data

(63) Continuation of application No. 13/702,890, filed as application No. PCT/NL2011/050416 on Jun. 9, 2011, now abandoned.

(30) Foreign Application Priority Data

Jun. 9, 2010   (NL) ..................................... 2004856

(51) Int. Cl.
*A61B 5/0428* (2006.01)
*A61B 5/04* (2006.01)
*A61B 5/00* (2006.01)

(52) U.S. Cl.
CPC ........ *A61B 5/04004* (2013.01); *A61B 5/0428* (2013.01); *A61B 5/7203* (2013.01); *A61B 2562/182* (2013.01)

(58) Field of Classification Search
CPC . A61B 5/04004; A61B 5/0428; A61B 5/7203; A61B 2562/182
See application file for complete search history.

(56) References Cited

U.S. PATENT DOCUMENTS 5,566,055 A * 10/1996 Salvi, Jr. .............. H05K 9/0037
174/358
5,851,191 A * 12/1998 Gozani ................ A61B 5/0488
600/554

(Continued)

FOREIGN PATENT DOCUMENTS

ES   WO 2009130338 A1 * 10/2009  ......... A61B 5/04004
WO   2009/130338         10/2009

OTHER PUBLICATIONS

International Search Report, Dated Jul. 19, 2011, in PCT/NL2011/050416.

*Primary Examiner* — Sean Dougherty
(74) *Attorney, Agent, or Firm* — NLO N.V.; Catherine A. Shultz; Minerva Rivero

(57) ABSTRACT

A measurement system for acquiring biopotentials is provided, which comprises a sensor device and a processing device, which are electrically connected to cooperate during use. The measurement system may be capable of simultaneous measurement of biopotentials by the sensor device and wireless transmission of amplified biopotentials by the processing device, and may be provided with means for preventing the measurements from being disturbed by the transmissions. Also disclosed are (i) a sensor device for measuring a biopotential having at least one sensor with a measurement electrode for measuring the biopotential at a measurement portion of a body and (ii) a processing device for processing biopotentials that has at least one sensor input for receiving the amplified biopotentials measured by a sensor of the sensor device.

15 Claims, 3 Drawing Sheets

(56) References Cited

U.S. PATENT DOCUMENTS

| | | | | |
|---|---|---|---|---|
| 2003/0052775 | A1* | 3/2003 | Shambroom | A61B 5/04004 340/539.1 |
| 2005/0165323 | A1* | 7/2005 | Montgomery | A61B 5/0006 600/544 |
| 2005/0215916 | A1 | 9/2005 | Fadem et al. | |
| 2008/0312523 | A1* | 12/2008 | Dunseath | A61B 5/04004 600/383 |
| 2010/0007413 | A1* | 1/2010 | Herleikson | A61B 5/0424 330/124 R |
| 2011/0001497 | A1* | 1/2011 | Chetelat | A61B 5/04004 324/692 |
| 2011/0295096 | A1* | 12/2011 | Bibian et al. | A61B 5/0478 600/372 |
| 2011/0295142 | A1* | 12/2011 | Chakravarthy | A61B 5/0476 600/544 |

* cited by examiner

SENSOR DEVICE, PROCESSING DEVICE, AND MEASUREMENT SYSTEM FOR ACQUIRING A BIOPOTENTIAL

TECHNICAL FIELD

The invention relates to a sensor device for measuring a biopotential, to a processing device for processing a biopotential, and to a measurement system for acquiring an amplified biopotential.

The invention further relates to a method of acquiring an amplified biopotential VP using a measurement system.

BACKGROUND

In modern healthcare, clinical measurements and medical data collection are abundantly performed on a patient in order to obtain information for medical research, diagnostic testing, early detection of critical illnesses and warning thereof, analysis of disease as well as monitoring the effect of medical treatment. In general terms, the purpose of clinical measurements is to collect information on the various body functions and or possible physiological conditions.

Information on body functions may for example be obtained by measuring the so called "biopotentials". A biopotential is an electric potential difference measured between two regions on, in, or near a patient's body.

An example of such a biopotential is the electrocardiogram (ECG). An ECG is a measurement in which the electrical conductivity of the nerve bundles located in the heart is determined. Due to the activity of the heart muscle, this conductivity varies in time. Based on obtained electrical signals representing the ECG, one can establish whether the temporal activity of the heart is normal or anomalous.

The ECG is obtained by applying a set of electrical sensors near, to, or inside of the patient's body. The electrical signal measured by the sensors is sent to a processing device. The sensor device and processing device combined form an acquisition system for measuring an ECG biopotential.

Other examples of biopotentials are the electromyogram (EMG), the electroencephalogram (EEG), the electrooculogram (EOG) and the vector cardiogram (VCG).

Commonly, biopotentials are measured by affixing several sensors with measuring electrodes to body regions of a patient. At least one sensor functions as a reference sensor. This reference sensor provides a reference potential measurement and is placed on a measurement portion of the patient body that is expected to be minimally electrically active. Subsequently, the potential difference between the reference sensor and any other sensor is determined. Alternatively, differences between the measured biopotential signals by pairs of sensors may be determined. Such a differential measurement is referred to as a "lead".

Measured potential differences are often very small, typically having a signal amplitude in the order of micro- to milliVolts. Therefore, distinguishing biopotential signals from the background electrical noise requires considerable signal processing.

Typically, the various sensors in the sensor device are connected to the processing device by means of electrically conducting cables. The sensor device transmits the measured biopotentials through the cables to the processing device, which processes the received biopotentials and possibly stores them in a buffer.

The biopotential signals measured with known systems are sensitive to various types of electrically induced noise. Capacitive effects and the tendency of the cables to act as receiving antennas for ambient EM fields may severely reduce the signal to noise ratio of the biopotentials. Capacitive coupling is caused by relative motion of the cables and the sensors that are attached to the patient's body. Random movement of a patient, e.g. during sleep or medical transport, may cause such effects. The interaction of RF-fields (e.g. from mobile phones) with the various components of the processing device constitutes an additional source of noise. Furthermore, ambient field sources operating at the mains supply frequencies, local temporary distortion of the common ground potential, or ground loop circular currents occurring between the patient's body and the processing device will all add further noise to the biopotential measurements.

SUMMARY

It is an object to provide a system for measuring biopotentials for which sensitivity of biopotential measurement to electromagnetically induced noise is reduced.

This object is achieved by a measurement system comprising a sensor device and a processing device as described by the claims, and designed to cooperate during use.

According to an aspect, there is provided a sensor device for measuring a biopotential Vp, wherein the sensor device comprises at least one sensor. The at least one sensor comprises a measurement electrode for measuring the biopotential Vp at a measurement portion of a body, and also comprises a measurement connection for a lead. The at least one sensor further comprises a first reference connection for receiving a reference potential $V_{ref}$, and a differential amplifier arranged for generating an amplified biopotential VP at a differential amplifier output by amplification of an electrical potential difference between the measured biopotential Vp and the reference potential $V_{ref}$. The differential amplifier output is connected to the measurement connection.

The sensor device may have several sensors as described here. Such a sensor with measurement electrode is able to measure a biopotential Vp at the measurement region of the body. The differential amplifier generates the amplified biopotential VP by amplifying the electric potential difference between the measured biopotential Vp and a reference potential Vref supplied via the reference connection. This amplified biopotential VP can be transmitted via the measurement connection, through a lead, to a connected processing device. By electrical amplification of the measured biopotential Vp near the sensor using the differential amplifier, a substantial portion of the intrinsic impedance of the sensor as well as the subsequent lead is effectively ignored. The resulting increase of voltage amplitude of the amplified biopotential VP prior to transmission through the lead yields an improved signal to noise ratio with respect to the capacitive noise generated within the leads.

According to an embodiment, there is provided a sensor device comprising a reference electrode with a second reference connection, arranged for supplying the reference potential $V_{ref}$ to a reference portion of the body.

By providing a separate reference electrode with a reference connection for receiving the reference potential Vref, any reference portion of the patient's body to which the reference potential will be applied can be selected at will. Setting the electrical reference potential to a fixed voltage value will suppress the noise induced by fluctuations of the common ground potential often used as reference for biopotential measurement.

According to an embodiment, the at least one sensor of the sensor device comprises a power connection for receiving a power signal for feeding the differential amplifier.

According to a further embodiment, the measurement connection, the first reference connection and the power connection of the sensor device are integrally formed and combined with the lead.

According to an embodiment, the differential amplifier in the at least one sensor of the sensor device comprises at least one RF-radiation hardened operational amplifier, arranged for shielding the at least one sensor from external EM RF fields.

By incorporating the RF-radiation hardened operational amplifier in the differential amplifier, the signal to noise ratio for the amplified biopotential VP is further improved, in particular with respect to noise generated within the at least one sensor by external EM RF field sources.

According to another aspect, there is provided a processing device for processing biopotentials, wherein the processing device comprises at least one sensor input for receiving an amplified biopotential VP measured by a sensor. The processing device is provided with a reference voltage source for generating a reference potential Vref and an amplifier power source for generating a power signal. The processing device further comprises at least one reference output and at least one power output, which are arranged for outputting the reference potential Vref and the power signal to a differential amplifier of the at least one sensor respectively.

The processing device is designed to cooperate in conjunction with the sensor device as previously described. The sensor device lead is arranged to be connected to the sensor input of the processing device during use, enabling the sensor device to supply the amplified biopotential VP to the processing device. In addition, the amplifier power source and the reference voltage source are able to feed the corresponding ports of the differential amplifier located in the sensor.

According to an embodiment, the processing device comprises a second reference output arranged for supplying the reference potential Vref to a reference electrode.

According to a further embodiment, the sensor input, the first reference output and the power output the processing device comprises are integrally formed as a sensor connection for each sensor.

According to an embodiment, the processing device comprises a communication unit arranged for wireless transmission of the amplified biopotential VP by means of EM RF fields.

Wireless transmission by the communication unit enables external parties concerned, like medical personnel with more powerful processing systems, to retrieve and analyze the measured biopotentials.

According to a further embodiment, the communication unit of the processing device is arranged for wireless transmission of the amplified biopotential VP by means of EM RF fields having frequencies principally in the GSM frequency bands.

According to another aspect, a measurement system for acquiring an amplified biopotential VP is provided, comprising a sensor device and a processing device according to embodiments described, wherein at least one sensor of the sensor device is electrically connected with at least one sensor input of the processing device by a lead during use.

According to an embodiment, the measurement system is arranged for simultaneous measurement of a biopotential Vp by the sensor device and wireless transmission of the amplified biopotential VP by the processing device according to embodiments described.

An amplified biopotential VP from the sensor device can then be wirelessly transmitted by the processing device, while simultaneously the sensor device continues measuring further biopotentials Vp without being interfered by the amplified biopotential VP transmission. This enables real time wireless transmission and live retrieval and analysis of the measured biopotentials by external parties concerned. No storing and batch sending of the amplified biopotentials VP and interruption of measurement of biopotentials VP is necessary, resulting in an improved access to up-to-date information.

According to an embodiment, the measurement system is arranged for receiving biopotential measurement instructions by the communication unit of the processing device, and for measuring the biopotential Vp according to the biopotential measurement instructions.

According to another aspect, there is provided a method of acquiring an amplified biopotential VP using a measurement system comprising a sensor device with at least one sensor having a differential amplifier. The measurement system further comprises a processing device with at least one sensor input. During use, the at least one sensor is electrically connected with the at least one sensor input. The method comprises measurement of a biopotential Vp at a measurement portion of a body using the at least one sensor. Furthermore, the method comprises the provision of a reference potential Vref to a reference portion of the body, and the provision of the measured biopotential Vp and the reference potential Vref to the differential amplifier. Subsequently the amplified biopotential VP is generated by the differential amplifier based on a potential difference between the measured biopotential Vp and the reference potential Vref.

According to an embodiment, the method comprises simultaneous measurement of the biopotential Vp using the at least one sensor, and wireless transmission of the amplified biopotential VP by RF EM fields, using the processing device comprising a communication unit.

BRIEF DESCRIPTION OF THE DRAWINGS

Embodiments will now be described, by way of example only, with reference to the accompanying schematic drawings in which corresponding reference symbols indicate corresponding parts, and in which.

The figures are only meant for illustrative purposes, and do not serve as restriction of the scope or the protection as laid down by the claims.

DETAILED DESCRIPTION

Figure 1:
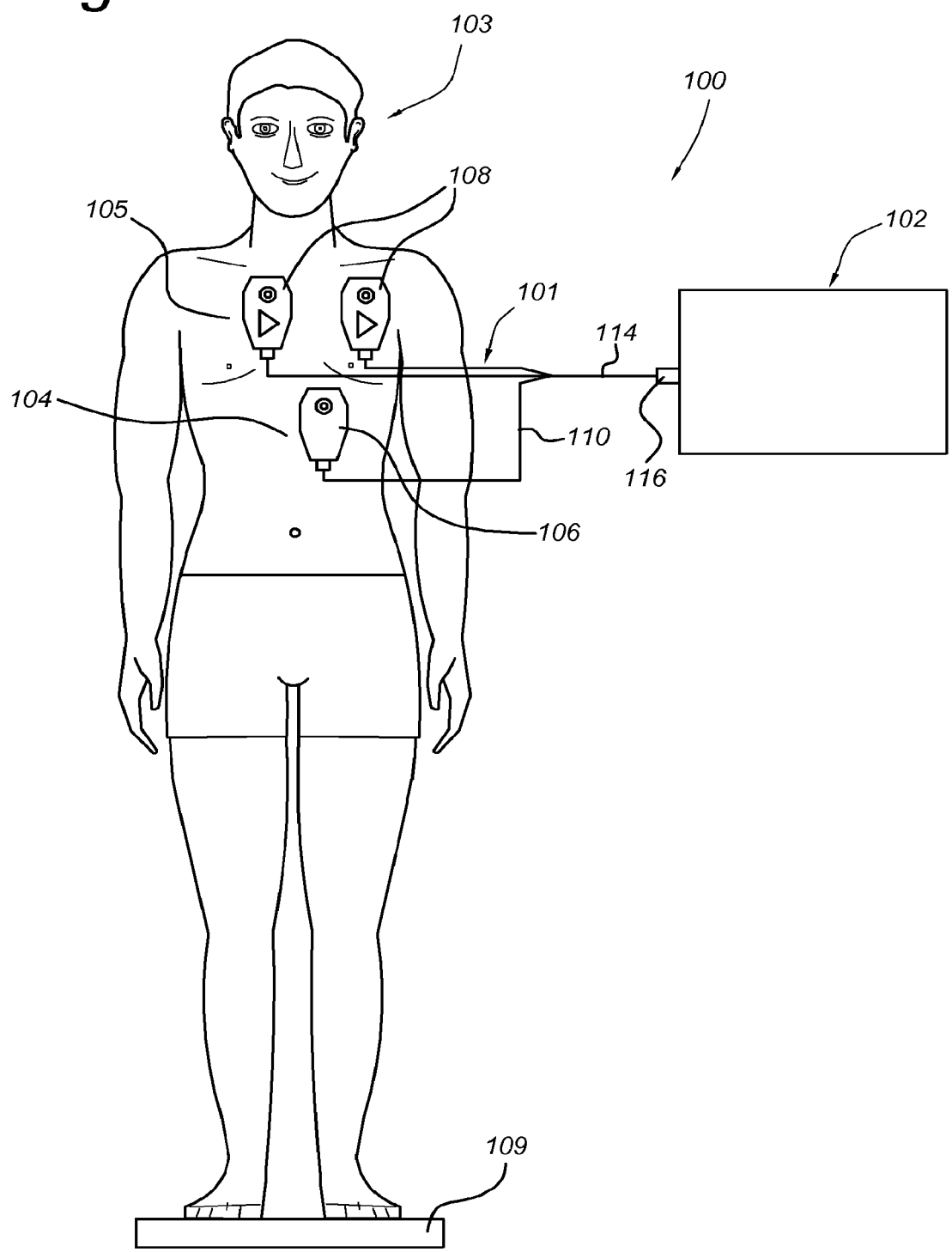
FIG. 1 schematically shows a measurement system according to an embodiment.

FIG. 1 schematically shows a measurement system 100 for acquiring an amplified biopotential VP according to an embodiment. Here, the general principles of the measurement system 100 are explained by using an ECG biopotential measurement system 100 as an example. The measurement system 100 comprises a sensor device 101 and a processing device 102. The sensor device 101 has at least one sensor 108 for measuring a biopotential Vp. The sensor 108 is attached to a measurement portion 105 of a patient's body 103 and able to measure the electrical biopotential Vb at the measurement portion 105. In the ECG measurement example, the sensors 108 measure the electrical conductivity of the nerve bundles located in the heart. During use of the measurement system 100, the sensor 108 is electrically connected to the processing device 102 by means of electrically conducting wiring forming a lead 110. The term "lead" is used here to indicate a bundle of one or more electrically conducting wires, arranged for connecting the biopotential measurement sensor 108 with the processing device 102. As was previously discussed, a "lead" may alternatively be interpreted as a difference between the measured biopotential signals of two selected sensors 108. Unless indicated otherwise, the first denotation of a lead is preferred here. The lead 110 may at the other end be connected to ports on the processing device 102. For convenience, the leads 110 may be joined into a single bundle of leads, which is referred to as a "lead cable" 114. Depending on the desired type of biopotential measurement, a varying number of sensors 108 and leads 110 may be required. For ECG measurements, sets of three, five, seven or ten leads are common. All leads 110 may be connectable by separate connectors to separate ports on the processing device 102. Alternatively, a single cable connector 116 provided at the end of the lead cable 114 may be connectable to an integrated port on the processing device 102.

The ECG biopotential measurement is obtained by attaching a set of sensors 108 near, on or inside of the patient's body 103. These sensors 108 exist in many varieties, the sticker electrode being a common one. This sticker electrode consists of a skin adhesive electrode layer and a small button for connecting to a coupling portion of an electrically conducting wire or lead 110. The conducting coupling portion of the biopotential sensor 108 between the lead 110 and the sticker electrode is commonly referred to as a "snap".

In FIG. 1 it is further shown that the sensor device 101 may have a reference snap 106 that is attachable to a reference portion 104 of the patient's body 103. This reference snap is arranged for providing an electric reference potential Vref at the reference portion 104.

In order to establish the reference potential Vref at the patient's body 103 independent of an ambient ground potential, the patient's body 103 may be electrically separated from the supporting surface by electrically insulating means 109. The addition of the reference snap 106 to the sensor device 101 will eliminate the unwanted distortions due to local fluctuations of the ambient ground potential. The sensor device 101 and processing device 102 are further explained with reference to FIGS. 2 and 3.

Figure 2A:
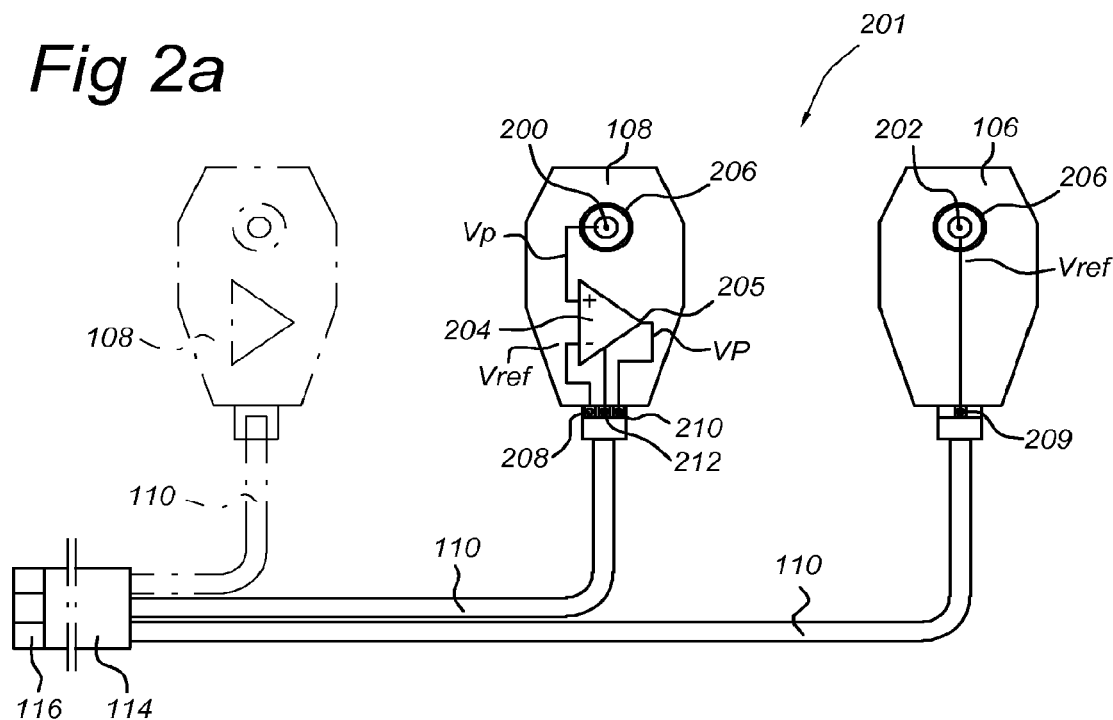
FIG. 2A presents a schematic view of a sensor device according to an embodiment.

FIG. 2A shows a schematic view of a sensor device 101 according to an embodiment. The sensor device 101 comprises at least one sensor 108. From the pair of sensors 108 depicted in FIG. 2A, only one is shown explicitly. The sensor 108 has a measurement electrode 200 for measuring a biopotential Vb at a region of contact. In FIG. 1 it was shown that the region of contact may be the measurement portion 105 of a patient's body 103.

The sensor 108 further comprises a first reference connection 208 for receiving the reference potential Vref. This Vref may be supplied by the processing device 102, or by other sources.

The sensor 108 has an integrated differential amplifier 204. The differential amplifier 204 is arranged for generating an amplified biopotential VB from a potential difference between the measured biopotential Vb and the reference potential Vref. This amplified biopotential VB is made available at a differential amplifier output 205.

The sensor 108 further has a measurement connection 210 in electrical contact with the differential amplifier output 205. This allows the signal of the differential amplifier output 205 to be transmitted through the lead 110.

As the differential amplifier 204 requires electrical power for operation, the sensor 108 may have a power connection 212 for receiving a power signal. The power may be obtained directly from the processing device 102, or from other sources.

As is shown in FIG. 2A, the measurement connection 210, the first reference connection 208 and the power connection 212 corresponding to one sensor 108 of the sensor device 101 may be integrally formed into one single lead 110. Multiple leads 110 from distinct sensors 108 may be joined into the lead cable 114 and may terminate in the cable connector 116.

The sensor device 101 may further have a reference electrode 202 arranged for supplying the reference potential Vref at the reference portion 104 of the body. As was discussed with reference to FIG. 1, this reference electrode 202 may be part of a reference snap 106. The reference snap 106 has a second reference connection 209 for receiving the reference potential Vref, which is in electrical contact with the reference electrode 202. The reference potential Vref may again be supplied by the processing device 102, or by other sources.

Via the second reference connection 209, the reference electrode 202 may be supplied with the reference potential Vref. For ECG measurements using skin attachable snaps, this Vref may typically be in the order of 1.5 V. By applying this reference potential Vref to a reference portion 104 of the body 103, unwanted emf's from circular currents locally generated in the near environment (yielding local distortion of the ground potential) may be suppressed.

The at least one sensor 108 may also be formed as a snap, being provided with a connection mechanism 206 for releasable connection to a disposable sticker electrode. The sticker electrode can be temporarily attached to reference or measurement portions 104, 105 of the skin. The method of connecting the sensors 108 to the patient's body 103 is not restricted to snaps with a button mechanism. Other more invasive type of sensors like needle shaped sensors 108 for subcutaneous placement or body implantable sensors 108 are possible.

The differential amplifier 204 in one sensor 108 of the sensor device 101 may comprise at least one radio frequency (RF) hardened operational amplifier 214 arranged for shielding the sensor 108 from external electromagnetic (EM) RF fields. The shielding may be particularly effective with respect to EM fields generated by wireless communication devices operating in the GSM frequency bands. Further optimization of the RF noise rejection in the sensor device 101 including the lead 110 may then be achieved by variation of the length of the lead 110, known to the skilled person.

Figure 2B:
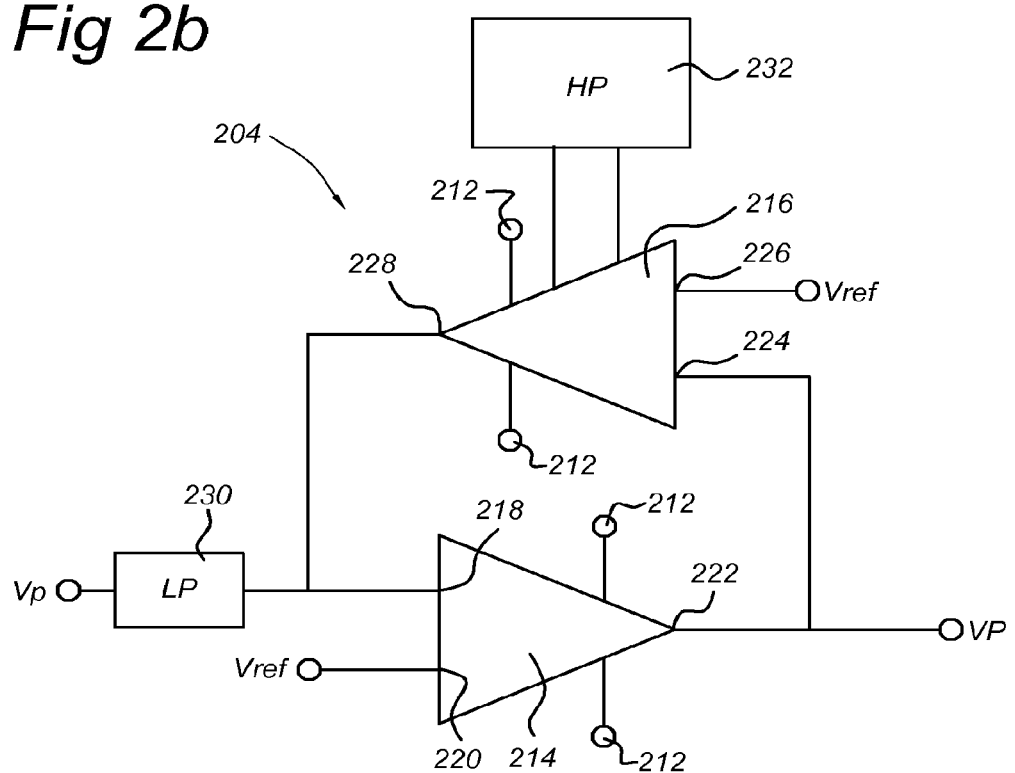
FIG. 2B displays an circuit diagram for the differential amplifier of the sensor device according to an embodiment.

FIG. 2B depicts an exemplary implementation of the differential amplifier 204 provided in the sensor 108. In the circuit shown here, the differential amplifier 204 has a first RF-hardened operational amplifier 214 for determining the potential difference between the measured biopotential Vp and the reference potential Vref. A low pass filter 230 may be provided, which is arranged to filter the measured biopotential Vp prior to entering the first operational amplifier 214 through a first operational amplifier input 218. A second RF-hardened operational amplifier 216 is connected with a second operational amplifier input 224 to a first operational amplifier output 222. A further first operational amplifier input 220 and a further second operational amplifier input 226 are connected to the first reference connection 210 of the sensor 108. This first reference connection 210 supplies the reference potential Vref to the further first operational amplifier input 220 and to the further second operational amplifier input 226. A second operational amplifier output 228 is connected in parallel with the original trace for the measured biopotential Vp, forming a feedback loop with the first RF-hardened operational amplifier 214. A high pass filter 232 may further be provided in the described circuit, for example in combination with the second operational amplifier 216, in order to remove unwanted high frequency noise. The resulting configuration schematically shown in FIG. 2B will significantly reduce the external EM RF field induced noise, preventing the noise from traversing the differential amplifier 204 and perturbing the amplified biopotential VP transmitted through the leads 110.

Figure 3:
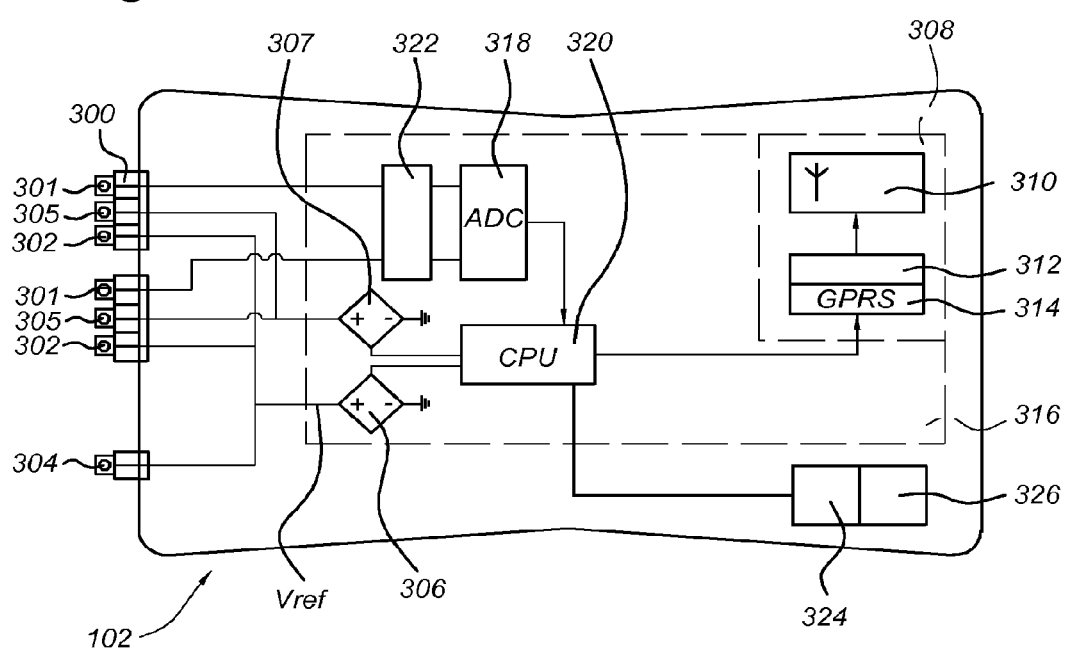
FIG. 3 illustrates a processing device according to an embodiment.

The leads 110 of the sensor device 101 are designed to be connectable to one or several ports of the processing device 102. The processing device 102 is a unit that may be capable of further processing, amplification, digitization, analysis and/or display of amplified biopotentials VP measured by the sensor device 101. FIG. 3 illustrates a processing device 102 for processing biopotentials. The processing device 102 shown has two sensor connections 300 for electrical communication with sensors 108 of the sensor system 101 as previously described. Any sensor connection 300 may comprise a sensor input 301 for receiving amplified biopotentials VP from one sensor 108.

In general, the processing device 102 may have one or several sensor connections 300. As shown, the processing device 102 may have a reference voltage source 306 for generating a reference potential $V_{ref}$ and an amplifier power source 307 for generating a power signal in accordance with the power requirements of the differential amplifiers 204 in the sensor device 101. The reference voltage source 306 may be provided with frequency rejection means for stabilizing the generated reference voltage Vref. The processing device 102 may further have a reference output 302 and a power output 305, paired with each sensor input 301. Each reference output 302 is arranged for outputting the reference potential $V_{ref}$ to one sensor 108 of the sensor device 101. Each power output 305 is arranged for outputting the power signal to the differential amplifier 204 of the sensor 108. The processing device 102 may further have a second reference output 304 for supplying the reference potential Vref to a reference electrode 106 of the sensor system 101.

Consequently, a measurement system 100 comprises a processing device 102 and a sensor device 101. During use, at least one sensor 108 of the sensor device 101 is electrically connected by a lead 110 to at least one sensor connection 300 of the processing device 102. As shown in FIG. 3, the sensor input 301, the first reference output 302 and the power output 305 may be integrally formed as single sensor connections 300 for each sensor 108. Moreover, several or all of the sensor inputs 301, first reference outputs 302, power outputs 305 and second reference output 304 may be combined into a joint port arranged to fit with the cable connector 116 provided on one end of the lead cable 114 of the sensor device 101.

The (analog) amplified biopotentials VP measured by the sensor device 101 are transmitted through the leads 110 and received by the processing device 102. The processing device 102 may be provided with a processing unit 320 for processing of the amplified biopotential signals. The processing unit 230 may be installed on a printed circuit board (PCB) 316 located in the processing device 102.

The amplified biopotentials VP may be first filtered with frequency decoupling means 322, which may also be provided on the PCB 316. The frequency decoupling means 322 are arranged to remove signal components outside of the expected frequency range characteristic to the biopotential signals (0.1 to 10 Hz). Subsequently, the filtered analog amplified signals may be converted to digital form by an analog-to-digital converter (ADC) 318, which may also be provided on the PCB 316. In addition, the processing unit 320 may be provided with further processing means.

The processing device may be provided with a device power source 324. This device power source 324 may be expendable, replaceable and/or rechargeable. The device power source 324 shown in FIG. 3 is integrally formed with the processing device 102. Alternatively, the device power source 324 may be a separate unit that is connectable to the processing device 102 by a power cord (not shown) and/or may comprise a battery unit 326.

The processing device 102 may be portable. As the processing device 102 is intended to be used for a few hours up-to many days, there is general acceptance for what is considered to be portable. One of the larger known portable biopotential processing devices used with patients is a mobile EMG recorder with a size of 15.8 cm×11 cm×7 cm and a weight of 770 grams. The current portable processing device 102 may have dimensions of 12 cm×6 cm×6 cm or smaller, and weigh less than 400 grams. The processing device 102 shown in FIG. 3 is approximately 10 cm×5 cm×5 cm and weighs approximately 200 grams. Such a portable processing device 102 may be body worn in a belt pouch or on a cord around the neck.

With such a relatively small size and weight, the portable processing device 102 is suitable for mobile application for unlimited periods of time, provided that the device power source 324 is recharged occasionally. Sustained portable use requires the processing device 102 to have low power consumption. The low power consumption and compactness of the components will restrict the processing capability of the portable processing device 102. As a result, only the most basic processing may be performed by the portable processing device 102. Advanced signal processing may subsequently be performed by computing devices that have more substantial processing capability and are not part of the processing device 102

It is desirable for the portable biopotential measurement system 100 to have wireless communication capability for transmitting the biopotential measurement to remote further processing devices, such as a computer of medically trained personnel. The processing device 102 may thus be arranged to transmit the processed biopotential measurements to a remote device for further processing and analysis (a computer, printer, telephone, or the like). The measurement system 100 may then be used for measurement of biopotentials for a patient residing outside of a medical hospital, while diagnostics and treatment planning can be performed from a remote location.

For this purpose, the processing device 102 may have a communication unit 308 arranged for wireless transmission of the amplified biopotential measurements by means of EM RF fields. The communication unit 308 shown in FIG. 3 constitutes an integral part of the processing device 102. Alternatively, the communication unit 308 may be formed as a separate unit that is connectable to the processing device 102 by electrical communication wiring (not shown).

Wireless transmission by the communication unit 308 may utilize Bluetooth™, WiFi™, GSM, GPRS, UMTS, HSDPA or other known wireless communication technologies. The communication unit 308 requires an antenna 310 for the transmission or reception of data carried by EM fields. The antenna 310 may then be optimized for the EM field frequencies corresponding to the relevant wireless communication technology used for transmission (i.e. 400-900 MHz and 1.8-1.9 GHz for GSM, 1.9-2.0 GHz and 2.1-2.2 GHz for UMTS, and 2.4 GHz and 5.0 GHz for WiFi). The communication unit 308 further requires a back end 314 and front end 312 for adapting the processed biopotential signal into transmittable form and actually converting it into EM radiation.

Wireless transmission may be achieved by utilizing the GSM frequency bands. The processing device 102 may therefore be arranged for wireless transmission of the amplified biopotential measurements by means of EM RF fields having frequencies principally in the GSM frequency bands. The communication unit 308 may then comprise a GSM module with a commercially obtainable GSM patch antenna 311 and GSM/GPRS modem 315 requiring a subscriber identity module (SIM).

The processing device 102, and in particular the communication unit 308, may further be arranged for simultaneous reception of biopotentials measured by the sensor device 101 and transmission of amplified biopotentials. Accordingly, the complete measurement system 100 may be arranged for simultaneous measurement of biopotentials Vp by the sensor device 101 and wireless transmission of amplified biopotentials VP by the processing device 102. The term "simultaneous" is used here to indicate that measurement of the biopotential Vp by the sensor device 101 can co-occur with wireless transmission of the amplified biopotential VP by the processing device 102. The amplified biopotential VP being transmitted may constitute a batched signal representing a buffered time sample of the measured biopotential Vp. The amplified biopotential VP being transmitted may also constitute a real time representation of the measured biopotential Vp, which will be further explained below. In any case, the measurement system 100 may be arranged such that the measurement of biopotentials Vp by the sensor device 101 may proceed, irrespective of the simultaneous wireless transmission of the amplified biopotentials VP by the processing device 102.

In particular, the processing device 102 with the communication unit 308, may be arranged for transmission of the amplified biopotentials VP in real time. The term "real time transmission" is used here to indicate the transmission of instantaneously measured and amplified biopotentials, without forming a batched measurement signal. The measurement of the biopotential Vp by the sensor system 101 occurs simultaneously with the real time transmission of the amplified biopotential VP by the processing device 102. This represents an alternative to the known "store and forward" method, in which a finite temporal sample of measured biopotentials is stored in a buffer, and only transmitted as batched data once measurement of biopotentials Vp is interrupted. In real time transmission, the signal may be transmitted virtually instantaneously, although possibly with a small signal processing delay.

Real time transmission is particularly beneficial for a portable processing device 102. As the portable processing device 102 is presumably restricted to low power consumption and processing capability, the portable processing device 102 preferably only performs basic processing. Advanced real time processing of the biopotential signals may then be performed by another processing device receiving the real time transmitted biopotential measurements. This may be only possible if the transmitted real time biopotentials are of relatively high quality i.e. have a high signal to noise ratio.

Without further measures, this wireless transmission generates additional noise within both the sensor device 101 (e.g. the conducting cables) and the processing device 102. These distortions are particularly troublesome when transmission of amplified biopotentials VP by the processing device 102 co-occurs with measurement of biopotentials Vp by the measurement device 101. These distortions occur in particular in portable biopotential measurement systems 100, as the compactness of the portable processing device 102 requires its electrical components to be small and closely spaced. EM fields with RF frequencies will significantly interfere with the electronic circuitry and components located within the measurement system 100. For example, the sensitivity of the leads 110 to EM fields strongly depends of the relation between the EM field frequencies and the length of the wire conductors within the leads 110. Wire shaped conductors with a length of several tens of centimeters up to one meter are especially sensitive to fields within the GSM frequency bands. The leads 110 and the components of both the sensor device 101 and the processing device 102 are therefore prone to distortion by the communication unit 308, or by ambient field sources (e.g. mobile phones).

Shielding of the sensors 108 from RF fields may be achieved by the already discussed RF hardened operational amplifiers 214, 216. In addition, the design of the PCB in the processing device 102 may be optimized for electromagnetic compatibility (EMC) of the distinct components and for shielding from radiation emanating from the communication unit 308. Digital and analog components located on the PCB 316 may be spatially separated in order to minimize electromagnetic interference (EMI). RF sensitive components and traces on the PCB 316 may be shielded from the radiation emanating from the antenna 310, by placement of the communication unit 308 with antenna 110 on one side of the PCB 316 and RF sensitive components on the other side of the PCB 316. The antenna 110 (e.g. GSM patch antenna 311) may have a highly directional radiation intensity profile. The gain maxima of the antenna 110 are preferably directed away from any sensitive components located on the PCB 316. Among these sensitive components are the reference voltage source 306 and the ADC 318, as well as further operational amplifiers and/or potential regulators. Dedicated reference potential ("grounding") planes may be provided within the PCB 316, in order to prevent the RF fields to traverse the PCB 316 and interfere with the sensitive components placed on the other side of the PCB 316. Highly sensitive traces located on the PCB 316 may further be enveloped by reference potential layers, lines, and/or planes.

In a portable processing device 102, the surface area of the PCB 316 is bound to be relatively small. A small PCB surface further reduces capacitive coupling between the components and traces on the PCB 316. A typical surface area for a PCB 316 used in the portable processing device 102 is 100 mm×40 mm.

The PCB 316 may have a multi layered configuration in order to achieve EM separation of the distinct digital signals, power signals and analog signals that are transmitted by the traces on the PCB 316.

Sensitive components on the PCB 316 may be provided with a relatively large metal casing, providing RF buffer functionality. The back end 314 of the communication unit 308 (e.g. a GSM modem or blue tooth module) may for example be encapsulated in such a metal casing.

The measurement system 100 may be arranged for receiving biopotential measurement instructions by the communication unit 308. Upon reception of measurement instructions, the measurement system 100 may execute the biopotential measurement according to these instructions. A remote device or operator may thus request for the measurement of a specific biopotential with respect to a desired body location or a comparison between body locations, within a preferred time window.

For this purpose, the communication unit 308 (e.g. comprising GSM/GPRS modem 315) may be arranged to communicate with the processing unit 320. Proper settings and communication may be executed by the processing unit 320. Communication between an operator and the processing device 102 may then be realized for example with an internet based server system.

The descriptions above are intended to be illustrative, not limiting. The particular placement of the sensors and the number of sensors and leads connecting the sensors to the processing device as illustrated in the figures merely serves as an example. A different number of sensors placed at various body locations is possible, as required by the information that is to be obtained from the biopotential measurements. Furthermore, the measurement system may be provided with additional non-biopotential based sensor types, a body temperature sensor, a finger clamp able mountable oxygen saturation sensor or a motion detector being examples.

It will be apparent to the person skilled in the art that alternative and equivalent embodiments of the invention can be conceived and reduced to practice, without departing from the scope of the claims set out below.

LIST OF FIGURE ELEMENTS 100 measurement system
101 sensor device
102 processing device
103 body
104 reference portion
105 measurement portion
106 reference snap
108 sensor
109 electrically insulating means
110 lead
114 lead cable
116 cable connector
Vref reference potential
Vb biopotential
VB amplified biopotential
200 measurement electrode
202 reference electrode
204 differential amplifier
205 differential amplifier output
206 connection mechanism
208 first reference connection
209 second reference connection
210 measurement connection
212 power connection
214 first operational amplifier
216 second operational amplifier
218 first operational amplifier input
220 further first operational amplifier input
222 first operational amplifier output
224 second operational amplifier input
226 further second operational amplifier input
228 second operational amplifier output
230 low pass filter
232 high pass filter
300 sensor connection
301 sensor input
302 first reference output
304 second reference output
305 power output
306 reference voltage source
307 amplifier power source
308 communication unit
310 antenna
311 GSM patch antenna
312 front end
314 back end
315 GSM/GPRS modem
316 printed circuit board
318 analog to digital converter
320 processing unit
322 frequency decoupling means
324 device power source
326 battery unit

The invention claimed is:

1. A device for measuring a biopotential Vp, comprising at least one sensor comprising:
   (i) a measurement electrode for measuring the biopotential Vp at a measurement portion of a body,
   (ii) a measurement connection for a lead,
   (iii) a first reference connection for receiving a reference potential Vref, and
   (iv) a differential amplifier connected to the measurement connection and arranged for generating an amplified biopotential VP at a differential amplifier output by amplification of an electrical potential difference between the measured biopotential Vp and the reference potential Vref, wherein the differential amplifier comprises
   a first operational amplifier with an input connected to the reference potential Vref,
   a second operational amplifier with an input connected to the reference potential Vref and a further input connected to an output of the first operational amplifier,
   wherein a second operational amplifier output is connected in parallel with the measured biopotential Vp, forming a feedback loop with the first operational amplifier,
   and wherein the differential amplifier further comprises a low-pass filter arranged to filter the biopotential Vp prior to entering the first operational amplifier, and a high-pass filter in combination with the second operational amplifier.

2. The device according to claim 1, further comprising a reference electrode with a second reference connection, arranged for supplying the reference potential Vref to a reference portion of the body.

3. The device according to claim 1, wherein the at least one sensor further comprises a power connection for receiving a power signal for feeding the differential amplifier.

4. The device according to claim 3, wherein the measurement connection, the first reference connection, and the power connection are integrally formed and combined with the lead.

5. The device according to claim 1, wherein the differential amplifier comprises at least one RF-radiation hardened operational amplifier arranged for shielding the at least one sensor from external EM RF fields.

6. A processing device for processing biopotentials, comprising:
(i) at least one sensor input for receiving an analog amplified biopotential VP measured by a sensor,
(ii) a reference voltage source for generating a reference potential Vref,
(iii) an amplifier power source for generating a power signal, and
(iv) at least one reference output and at least one power output, which are arranged for outputting the reference potential Vref to a differential amplifier and the power signal to the sensor, the differential amplifier comprises a first operational amplifier with an input connected to the reference potential Vref,
a second operational amplifier with an input connected to the reference potential Vref and a further input connected to an output of the first operational amplifier,
wherein a second operational amplifier output is connected in parallel with the measured biopotential Vp, forming a feedback loop with the first operational amplifier,
and wherein the differential amplifier further comprises a low-pass filter arranged to filter the biopotential Vp prior to entering the first operational amplifier, and a high-pass filter in combination with the second operational amplifier.

7. The processing device according to claim 6, further comprising a second reference output arranged for supplying the reference potential Vref to a reference electrode.

8. The processing device according to claim 6, wherein the sensor input, a first reference output, and the power output are integrally formed as a sensor connection for each sensor.

9. The processing device according to claim 6, further comprising a communication unit arranged for wireless transmission of the amplified biopotential VP by EM RF fields.

10. The processing device according to claim 9, wherein the EM RF fields have frequencies in GSM frequency bands.

11. A measurement system for acquiring an amplified biopotential VP, comprising:
(a) a sensor device comprising at least one sensor comprising (i) a measurement electrode for measuring the biopotential Vp at a measurement portion of a body, (ii) a measurement connection for a lead, (iii) a first reference connection for receiving a reference potential Vref, and (iv) a differential amplifier connected to the measurement connection and arranged for generating an amplified biopotential VP at a differential amplifier output by amplification of an electrical potential difference between the measured biopotential Vp and the reference potential Vref, and
(b) a processing device comprising (i) at least one sensor input for receiving an analog amplified biopotential VP measured by a sensor, (ii) a reference voltage source for generating a reference potential Vref, (iii) an amplifier power source for generating a power signal, and (iv) at least one reference output and at least one power output, which are arranged for outputting the reference potential Vref and the power signal to a differential amplifier of the sensor, respectively,
wherein at least one sensor of the sensor device is electrically connected with at least one sensor input of the processing device by a lead during use, and
wherein the differential amplifier comprises
a first operational amplifier with an input connected to the reference potential Vref,
a second operational amplifier with an input connected to the reference potential Vref,
wherein a further input of the second operational amplifier is connected to an output of the first operational amplifier,
wherein a second operational amplifier output is connected in parallel with the measured biopotential Vp, forming a feedback loop with the first operational amplifier,
and wherein the differential amplifier further comprises a low-pass filter arranged to filter the biopotential prior to entering the first operational amplifier, and a high-pass filter in combination with the second operational amplifier.

12. The measurement system according to claim 11, arranged for simultaneous measurement of a biopotential Vp by the sensor device and wireless transmission of the analog amplified biopotential VP by the processing device by EM RF fields.

13. The measurement system according to claim 11, arranged for receiving biopotential measurement instructions by the communication unit of the processing device by EM RF fields, and for measuring the biopotential Vp according to the biopotential measurement instructions.

14. A method of acquiring an amplified biopotential VP with a measurement system comprising (i) a sensor device comprising at least one sensor with a differential amplifier, and (ii) a processing device comprising at least one sensor input, wherein during use, the at least one sensor is electrically connected with the at least one sensor input, wherein the differential amplifier comprises
a first operational amplifier with an input connected to the reference potential Vref,
a second operational amplifier with an input connected to the reference potential Vref,
wherein a further input of the second operational amplifier is connected to an output of the first operational amplifier,
wherein a second operational amplifier output is connected in parallel with the measured biopotential Vp, forming a feedback loop with the first operational amplifier,
and wherein the differential amplifier fluffier comprises a low-pass filter arranged to filter die biopotential Vp prior to entering the first operational amplifier, and a high-pass filter in combination with the second operational amplifier,
the method comprising measuring a biopotential Vp at a measurement portion of a body using the at least one sensor by
(a) providing a reference potential Vref to a reference portion of the body;
(b) providing the measured biopotential Vp and the reference potential Vref to the differential amplifier; and
(c) generating the amplified biopotential VP by the differential amplifier based on a potential difference between the measured biopotential Vp and the reference potential Vref.

15. The method according to claim 14, comprising simultaneously measuring the biopotential Vp using the at least one sensor, and wireless transmission of the analog amplified biopotential VP by RF EM fields, using the processing device comprising a communication unit.

\* \* \* \* \*